United States Patent
Carlsson et al.

(10) Patent No.: US 12,036,038 B2
(45) Date of Patent: Jul. 16, 2024

(54) OSTOMY APPLIANCE COMPRISING THERMAL SENSORS

(71) Applicant: Hollister Incorporated, Libertyville, IL (US)

(72) Inventors: Jonas P. Carlsson, Chicago, IL (US); Michael P. Nolan, Chicago, IL (US); Christina Augustyn, Chicago, IL (US); James Brandon Barker, Antioch, IL (US); Ryan S. Park, Northbrook, IL (US); Scott Janis, El Cerrito, CA (US); Stephanie Henze, San Mateo, CA (US); Christopher Michael Wlezien, Evanston, IL (US); Somasunder Vijay Sekaran, San Francisco, CA (US); Germain Verbrackel, San Francisco, CA (US); Robert Lane, Larkspur, CA (US); Scott E. Liddle, Raleigh, NC (US); Stephanie Musinsky, Raleigh, NC (US); Kyle A. Matthews, Chapel Hill, NC (US)

(73) Assignee: HOLLISTER INCORPORATED, Libertyville, IL (US)

(*) Notice: Subject to any disclaimer, the term of this patent is extended or adjusted under 35 U.S.C. 154(b) by 721 days.

(21) Appl. No.: 17/282,938

(22) PCT Filed: Oct. 3, 2019

(86) PCT No.: PCT/US2019/054496
§ 371 (c)(1),
(2) Date: Apr. 5, 2021

(87) PCT Pub. No.: WO2020/076609
PCT Pub. Date: Apr. 16, 2020

(65) Prior Publication Data
US 2021/0386368 A1    Dec. 16, 2021

Related U.S. Application Data

(60) Provisional application No. 62/807,504, filed on Feb. 19, 2019, provisional application No. 62/743,261, filed on Oct. 9, 2018.

(51) Int. Cl.
*A61B 5/00* (2006.01)
*A61F 5/443* (2006.01)
(Continued)

(52) U.S. Cl.
CPC .......... *A61B 5/4851* (2013.01); *A61B 5/0008* (2013.01); *A61F 5/443* (2013.01);
(Continued)

(58) Field of Classification Search
CPC ................ A61B 5/4851; A61B 5/0008; A61B 2562/0271; A61F 5/443; C08L 33/10; C08L 75/04
See application file for complete search history.

(56) References Cited

U.S. PATENT DOCUMENTS 5,862,204 A    1/1999   Kim et al.
7,607,823 B2   10/2009  Kent
(Continued)

FOREIGN PATENT DOCUMENTS

CN    207152693 U  *  3/2018
CN    207152693 U     3/2018
(Continued)

OTHER PUBLICATIONS

International Search Report issued by ISA/EPO in connection with PCT/US2019/054496 on Jan. 9, 2020.
(Continued)

*Primary Examiner* — Benjamin J Klein
*Assistant Examiner* — Rachel O'Connell
(74) *Attorney, Agent, or Firm* — Klintworth & Rozenblat IP LLP

(57) ABSTRACT

An ostomy appliance system includes an ostomy appliance having a stoma opening and a first electrical interface, and at least one thermal sensor configured to detect at least one thermal property, such as temperature, at the ostomy appliance, the at least one temperature sensor connected to the first electrical interface with electrical circuitry. A wearable device may be removably connected to the ostomy appliance and operably connected to the at least one thermal sensor. The wearable device includes a housing, a second electrical
(Continued)

interface configured for electrical connection to the first electrical interface, a power supply and a controller operably connected to the power supply. The controller is configured to determine a condition of the ostomy appliance based on the at least one thermal property detected at the at least one thermal sensor. The wearable device may also include a wireless transceiver configured to communicate with a personal communication device.

22 Claims, 12 Drawing Sheets

(51) Int. Cl.
  *C08L 33/10* (2006.01)
  *C08L 75/04* (2006.01)
(52) U.S. Cl.
  CPC .............. *C08L 33/10* (2013.01); *C08L 75/04* (2013.01); *A61B 2562/0271* (2013.01)

(56) References Cited

U.S. PATENT DOCUMENTS

| | | | |
|---|---|---|---|
| 9,372,123 | B2 | 6/2016 | Li et al. |
| 2004/0067481 | A1 | 4/2004 | Leonard et al. |
| 2010/0030167 | A1 | 2/2010 | Thirstrup et al. |
| 2014/0051946 | A1 | 2/2014 | Arne |
| 2014/0238398 | A1* | 8/2014 | Christopher .......... A61B 5/087 128/204.22 |
| 2015/0182159 | A1 | 7/2015 | Sella |
| 2017/0140103 | A1* | 5/2017 | Angelides ............. A61F 5/4404 |
| 2019/0142623 | A1 | 5/2019 | Norman et al. |
| 2019/0240059 | A1 | 8/2019 | Michael et al. |
| 2020/0000624 | A1 | 1/2020 | Jennifer et al. |
| 2020/0246174 | A1 | 8/2020 | Ask et al. |
| 2020/0246175 | A1 | 8/2020 | Ask et al. |
| 2020/0246176 | A1 | 8/2020 | Ask et al. |
| 2020/0246177 | A1 | 8/2020 | Ask et al. |
| 2021/0275341 | A1* | 9/2021 | Hansen ................. A61F 5/4404 |
| 2021/0353448 | A1 | 11/2021 | George et al. |
| 2021/0369491 | A1 | 12/2021 | Holden |
| 2022/0117771 | A1 | 4/2022 | Fearn et al. |
| 2022/0257405 | A1 | 8/2022 | Peder et al. |
| 2022/0265457 | A1 | 8/2022 | Jonas et al. |
| 2022/0313473 | A1 | 10/2022 | Olav et al. |
| 2023/0031979 | A1 | 2/2023 | Stendevad et al. |

FOREIGN PATENT DOCUMENTS

| | | | | |
|---|---|---|---|---|
| GB | 2431239 | A | | 4/2007 |
| WO | 2007098762 | A1 | | 9/2007 |
| WO | 2017023794 | A1 | | 2/2017 |
| WO | WO-2017023794 | A1 | * | 2/2017 ........... A61B 10/007 |
| WO | 2018028756 | A1 | | 2/2018 |
| WO | 2019/094635 | A1 | | 5/2019 |
| WO | 2019/120424 | A1 | | 6/2019 |
| WO | 2019/120425 | A1 | | 6/2019 |
| WO | 2019/120426 | A1 | | 6/2019 |
| WO | 2019/120427 | A1 | | 6/2019 |
| WO | 2019/120428 | A1 | | 6/2019 |
| WO | 2019/120429 | A1 | | 6/2019 |
| WO | 2019/120430 | A1 | | 6/2019 |
| WO | 2019/120432 | A1 | | 6/2019 |
| WO | 2019/120433 | A1 | | 6/2019 |
| WO | 2019/120434 | A1 | | 6/2019 |
| WO | 2019/120435 | A1 | | 6/2019 |
| WO | 2019/120436 | A1 | | 6/2019 |
| WO | 2019/120437 | A1 | | 6/2019 |
| WO | 2019/120440 | A1 | | 6/2019 |
| WO | 2019/120441 | A1 | | 6/2019 |
| WO | 2019/120442 | A1 | | 6/2019 |
| WO | 2019/120443 | A1 | | 6/2019 |
| WO | 2019/120444 | A1 | | 6/2019 |
| WO | 2019/120445 | A1 | | 6/2019 |
| WO | 2019/120446 | A1 | | 6/2019 |
| WO | 2019/120448 | A1 | | 6/2019 |
| WO | 2019/120449 | A1 | | 6/2019 |
| WO | 2019/120450 | A1 | | 6/2019 |
| WO | 2019/120451 | A1 | | 6/2019 |
| WO | 2019/120452 | A1 | | 6/2019 |
| WO | 2019/120453 | A1 | | 6/2019 |
| WO | 2019/120458 | A1 | | 6/2019 |
| WO | 2019/149330 | A1 | | 8/2019 |
| WO | 2019/161859 | A1 | | 8/2019 |
| WO | 2019/161860 | A1 | | 8/2019 |
| WO | 2019/161861 | A1 | | 8/2019 |
| WO | 2019/161862 | A1 | | 8/2019 |
| WO | 2019/161863 | A1 | | 8/2019 |
| WO | 2019/174687 | A1 | | 9/2019 |
| WO | 2019/174692 | A1 | | 9/2019 |
| WO | 2019/174693 | A1 | | 9/2019 |
| WO | 2019/174694 | A1 | | 9/2019 |
| WO | 2019/174695 | A1 | | 9/2019 |
| WO | 2019/174696 | A1 | | 9/2019 |
| WO | 2019/174697 | A1 | | 9/2019 |
| WO | 2019/174698 | A1 | | 9/2019 |
| WO | 2019/174699 | A1 | | 9/2019 |
| WO | 2019/238180 | A1 | | 12/2019 |
| WO | 2019/238181 | A1 | | 12/2019 |
| WO | 2019/238182 | A1 | | 12/2019 |
| WO | 2019/238183 | A1 | | 12/2019 |
| WO | 2020/035121 | A1 | | 2/2020 |
| WO | 2020/123771 | A2 | | 6/2020 |
| WO | 2020/156624 | A1 | | 8/2020 |
| WO | 2020/156625 | A1 | | 8/2020 |
| WO | 2020/156626 | A1 | | 8/2020 |
| WO | 2020/169162 | A1 | | 8/2020 |
| WO | 2020/173534 | A1 | | 9/2020 |
| WO | 2020/216426 | A1 | | 10/2020 |
| WO | 2020/216427 | A1 | | 10/2020 |
| WO | 2020/216429 | A1 | | 10/2020 |
| WO | 2020/259775 | A1 | | 12/2020 |
| WO | 2021/063463 | A1 | | 4/2021 |
| WO | 2021/063466 | A1 | | 4/2021 |
| WO | 2021/165703 | A1 | | 8/2021 |
| WO | 2021/165705 | A1 | | 8/2021 |
| WO | 2021/185425 | A1 | | 9/2021 |
| WO | 2021/209104 | A1 | | 10/2021 |
| WO | 2022/063379 | A1 | | 3/2022 |
| WO | 2022/078561 | A1 | | 4/2022 |
| WO | 2022/207049 | A1 | | 10/2022 |

OTHER PUBLICATIONS

Written Opinion issued by ISA/EPO in connection with PCT/US2019/054496 on Jan. 9, 2020.

International Preliminary Report on Patentability issued by ISA/EPO in connection with PCT/US2019/054496 on Apr. 8, 2021.

* cited by examiner

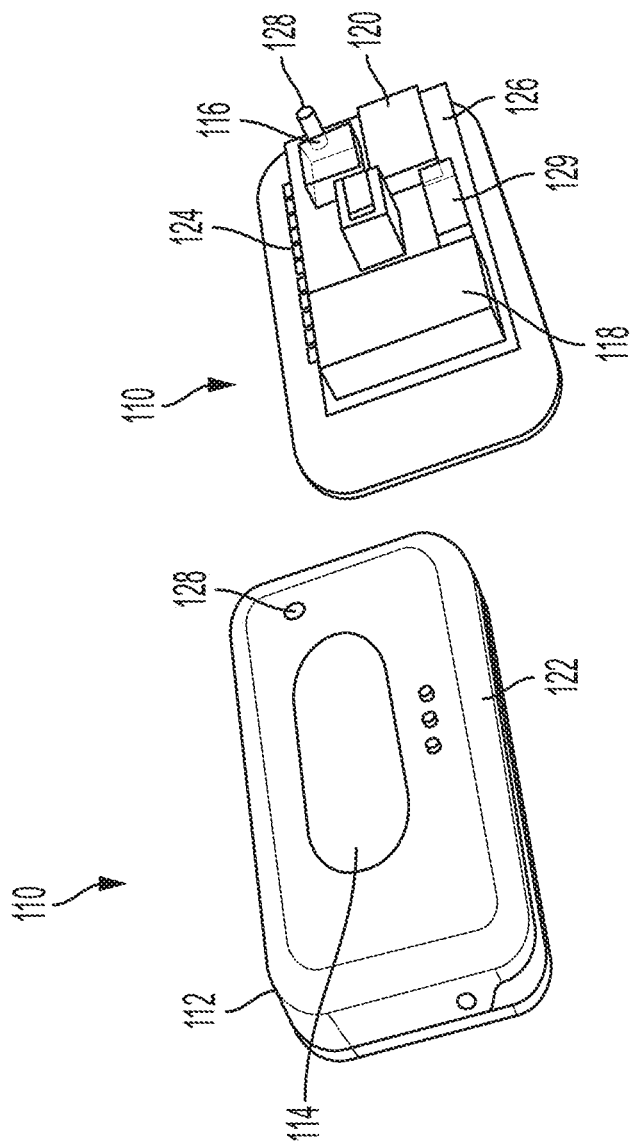

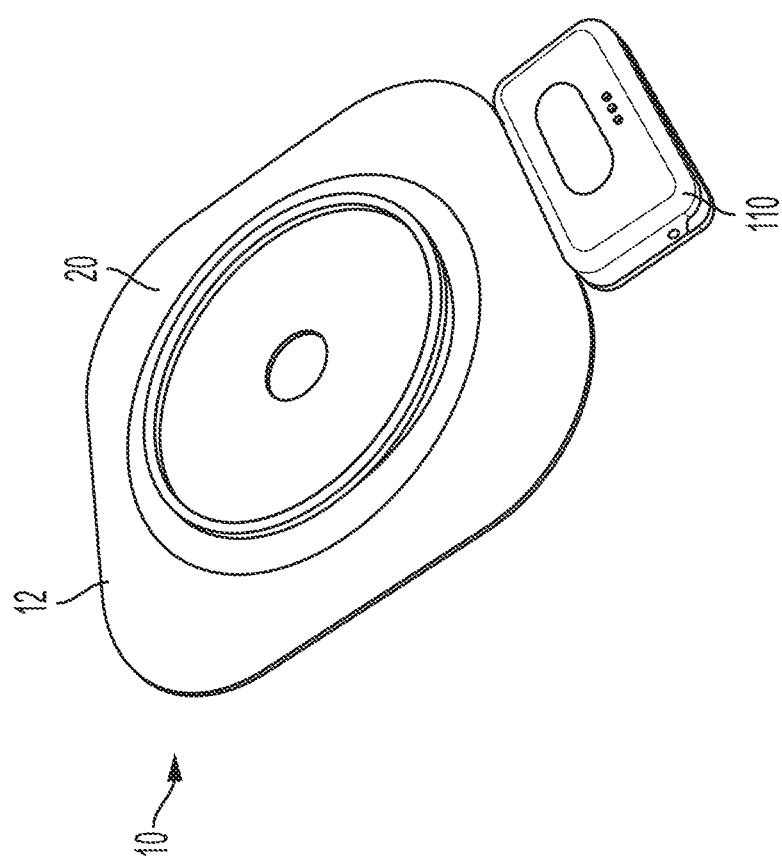

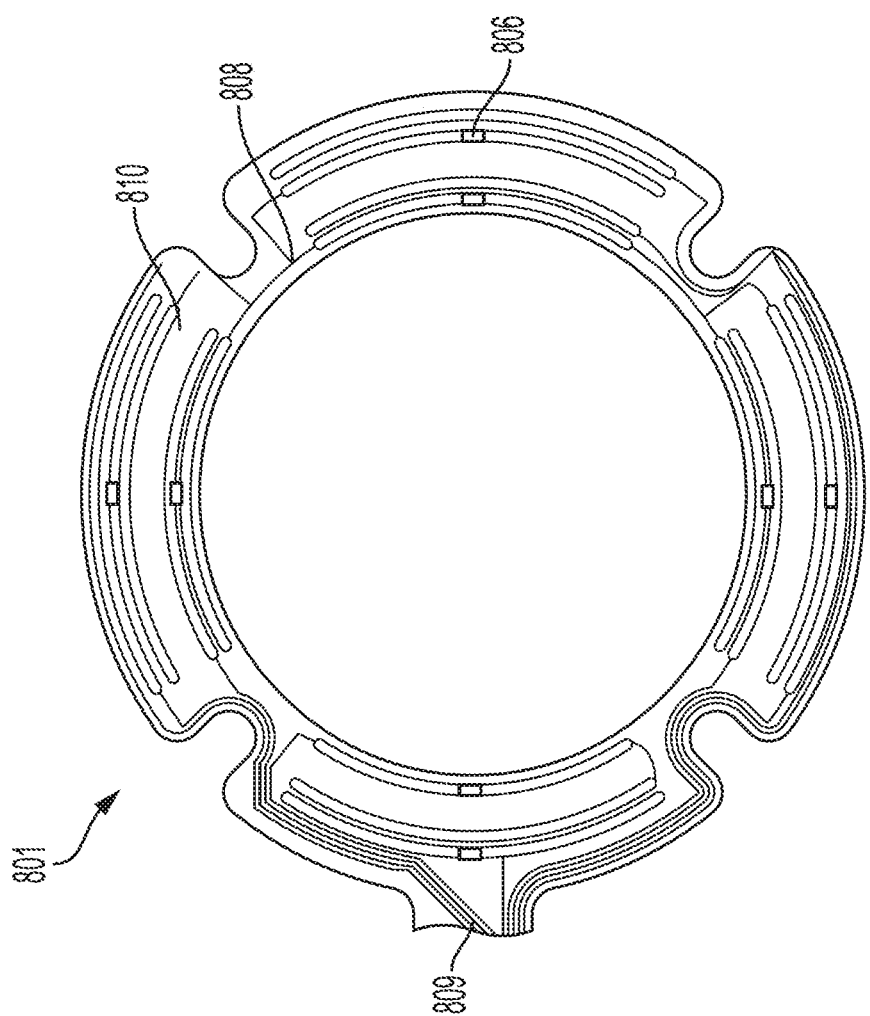

OSTOMY APPLIANCE COMPRISING THERMAL SENSORS

This is a National Stage Application of International Patent Application No. PCT/US2019/054496, filed Oct. 3, 2019, which claims the benefit of and priority to U.S. Provisional Application No. 62/743,261 filed Oct. 9, 2018 and U.S. Provisional Application No. 62/807,504, filed Feb. 19, 2019, the entireties of which are incorporated fully herein by reference.

BACKGROUND

The following description relates generally to an ostomy appliance configured for thermal property-based condition monitoring.

An ostomy pouch includes opposing sidewalls defining an internal collection area. One of the sidewalls is provided with an inlet opening to receive a stoma, and means to secure the pouch to the user. Such means include, for example, an ostomy barrier, faceplate or barrier ring which may be connected to or formed integrally with the sidewall having the inlet opening. The ostomy barrier (or faceplate or barrier ring) may include adhesive on a skin-facing side to seal against the user's skin in an area surrounding the stoma. Such a system is intended to prevent or limit leakage of bodily fluid discharged from the stoma through the stoma/barrier/pouch environment.

However, the seal formed between the ostomy barrier and the user may weaken, for example, with time, movement, improper installation and/or application of an external force, and thus, become susceptible to leaking. Often times, the user is unaware of or cannot easily assess an extent of weakening in the seal. Thus, a user is typically not aware of a weakened seal, and consequently, the risk of leakage, until a fluid discharged from the stoma leaks through to an exterior of the seal (i.e., the barrier) and becomes undesirably exposed to an external environment outside of the stoma/barrier/pouch environment.

Efforts have been made to detect leakage of fluid in urological environments based on temperature. For example, U.S. Pat. No. 5,862,204 discloses a leakpoint wetness sensor for urological investigations including an instrument having a passage to pass a catheter intended for insertion into the bladder through the urethra. A temperature sensitive reference sensor is mounted to the body and is exposed to and responsive to ambient temperature. A receptacle in the body is disposed and arranged to receive liquid leaking from the urethra past the catheter. A temperature sensitive detector sensor is mounted to the body where it will be contacted by the leaked liquid and the detector sensor is responsive to the temperature of the liquid. A circuit device is responsive to outputs from the sensors to provide a response reflective of a difference between the temperatures when the detector sensor is wetted by leaked liquid.

U.S. Pat. No. 7,607,823 relates to a system and method for detecting leaks and includes a sensing circuit having a first thermistor device adapted to detect a leak upon contact with a liquid, and a second thermistor device functioning as a reference device. The first and second thermistor devices are driven with a current such that both devices operate in self-heated mode at a temperature above an ambient temperature. A control system controls a drive circuit for maintaining a constant application of power through both devices in response to a voltage monitored at a reference point in the sensing circuit including the reference thermistor. The voltage at a reference point in a portion of the sensing circuit including the first thermistor device is additionally monitored and compared with the voltage at the reference point in the sensing circuit including the second thermistor device. A leak condition is determined on the basis of a comparison result of the ambient temperature.

U.S. Pat. No. 9,372,123 relates to systems, methods, apparatuses and devices for monitoring a property of an object or an individual, using a conformal sensor device that substantially conforms to contours of a portion of a surface of the object or the individual. The measurement includes data indicative of a property of a temperature of the portion of the surface and the degree of the conformal contact. An analysis engine is used to analyze the data and to generate at least one parameter indicative of the property of the temperature. Based on a comparison of the at least one parameter to a preset threshold, at least one alert can be issued and/or a command can be transmitted to regulate an environmental condition. The at least one alert can be indicative of a potential risk of harm to the object or individual.

Further, US Pat. Application Publication No. 2004/0067481 discloses a thermal sensor for fluid detection including thermistors operating in a self-heating mode. US Pat. Application Publication No. 2015/0182159 discloses an apparatus for determining a flow rate of body fluid including at least one thermistors, wherein the apparatus calculates the fluid flow rate based on differences between electrical signals from the thermistors. However, none of the above-described references provides for thermal property-based condition monitoring of an ostomy appliance.

Accordingly, it is desirable to provide an ostomy appliance, such as an ostomy skin barrier or ostomy pouch having such an ostomy skin barrier, in which a condition may be monitored based on a detected thermal property, such as temperature. It is also desirable to provide an ostomy appliance in which a notification may be provided to the user based on the monitored condition.

SUMMARY

In one aspect, an ostomy appliance may comprise a skin barrier, at least one thermal sensor configured to detect at least one thermal property of the ostomy appliance, and a first electrical interface. The at least one thermal sensor may be connected to the first electrical interface via an electrical circuitry. The at least one thermal sensor may comprise a plurality of temperature sensors or a plurality of thermistors that are configured to detect at least one thermal property of the skin barrier material. In some embodiments, the plurality of thermistors may be configured to operate in a self-heating mode.

In another aspect, an ostomy appliance may comprise a skin barrier and a leak detection system attached to the skin barrier. The leak detection system may comprise at least one thermistor configured to operate in a self-heating mode to measure a change in temperature ($\Delta T$) of the ostomy appliance and a first electrical interface, wherein the at least one thermistor is connected to the first electrical interface via an electrical circuitry. The skin barrier may be formed from a hydrocolloid adhesive.

In an embodiment, the leak detection system may be configured to apply a voltage to the at least one thermistor at one or more polling frequencies. The at least one thermistor may be configured to transfer heat to the skin barrier, wherein the heat capacity of the skin barrier is greater when wet than dry, such that the $\Delta T$ of the skin barrier when dry is greater than when wet. In some embodiments, the ostomy appliance may further include at least one wicking material arranged proximate the at least one thermal sensor. In such embodiments, the at least one thermistor may be configured to transfer heat to the wicking material, wherein the heat capacity of the wicking material is greater when wet than dry, such that the ΔT of the wicking material when dry is greater than when wet. The leak detection system may be configured to determine a leak based on a drop in the ΔT of the skin barrier and/or the wicking material.

In an embodiment, the leak detection system may be configured to transfer heat to measure the ΔT of about 6° C. to about 11° C. when the skin barrier or the wicking material is dry. The leak detection system may be configured to apply a voltage to the at least one thermistor for a duration of about 1 second at a polling frequency of about once every 30 seconds to once every 15 minutes. In some embodiments, the leak detection system may be configured to allow a user to set and change the polling frequency.

In an embodiment, the at least one thermistor may be embedded in the skin barrier. The at least one thermistor may include a plurality of thermistors operating in a self-heating mode. The ostomy appliance may also include a plurality of wicking materials, wherein the plurality of thermistors and the plurality of wicking materials are embedded in the skin barrier. Each of the plurality of wicking materials may be arranged adjacent each of the plurality of thermistors, such that each of the plurality of wicking materials is in contact with user's skin when the ostomy appliance is attached to a user. An electrical circuit may be provided adjacent each of the plurality of thermistors.

In an embodiment, the at least one thermistor may be coated with a conformal coating. The conformal coating may be formed from a blend of urethane oligomer and (meth)acrylate monomer and have a thickness of about 20 microns to about 100 microns.

The ostomy appliance may include a stoma opening for receiving a stoma, and the at least one thermistor may include a plurality of thermistors. In an embodiment, the plurality of thermistors may be positioned along a path concentric with the stoma opening. In another embodiment, the plurality of thermistors may be positioned along a plurality of paths concentric with the stoma opening. The plurality of paths may be disposed at different distances from the stoma opening.

In an embodiment, the ostomy appliance may be a faceplate for a two-piece ostomy pouch system including a body-side coupling ring configured to engage with a pouch-side coupling ring provided on an ostomy pouch to attach the ostomy pouch to the faceplate. In another embodiment, the ostomy appliance may be an ostomy skin barrier appliance for a one-piece ostomy pouch system attached to an ostomy pouch. In yet another embodiment, the ostomy appliance may be an ostomy skin barrier ring.

The ostomy appliance may further include a wearable device removably and operably connected to the leak detection system. The wearable device may include a housing, a second electrical interface configured for electrical connection to the first electrical interface, a power supply, and a controller operably connected to the power supply.

In an embodiment, the controller may be configured to determine a condition of the ostomy appliance based on the at least one thermal property detected at the at least one thermal sensor. For example, the controller may determine an ostomy effluent leakage condition based on a change in the at least one thermal property of the barrier material from exposure to an ostomy effluent or an ostomy appliance detachment condition based on a change in a temperature of the barrier material due to detachment of the barrier material from a user. In an embodiment, the controller may be configured to determine an ostomy effluent leakage condition based on a change in the ΔT from exposure to an ostomy effluent or an ostomy appliance detachment condition based on a change in the ΔT due to detachment of the skin barrier from a user. The wearable device may further include one or more output devices operably connected to the controller and configured to output a notification based on the determined condition. The wearable device may also include a wireless transceiver.

According to an embodiment, the ostomy appliance may further include a personal communication device communicatively connected to the wearable device via the wireless transceiver. The personal communication device may be configured to output a notification based on a condition of the ostomy appliance. The personal communication device may be a smartphone.

Other aspects, objectives and advantages will become more apparent from the following detailed description.

BRIEF DESCRIPTION OF THE DRAWINGS

FIG. 4 is a perspective view of a wearable device of the ostomy appliance, according to an embodiment;

FIG. 5 is a cut-away perspective view of the wearable device of FIG. 4, according to an embodiment;

FIG. 6 is a perspective view of the ostomy appliance having the wearable device connected to an ostomy hydrocolloid, according to an embodiment;

FIG. 16 is a schematic illustration of the leak detection system of FIG. 15.

DETAILED DESCRIPTION

Figure 2:
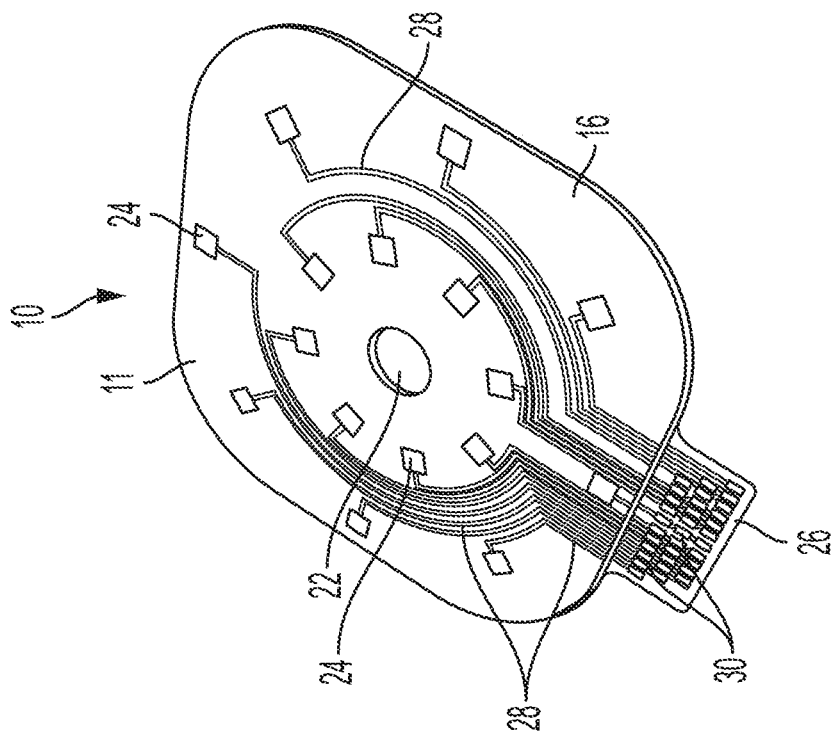
FIG. 2 is a perspective view of a body-facing side of the ostomy appliance, according to an embodiment.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

Figure 1:
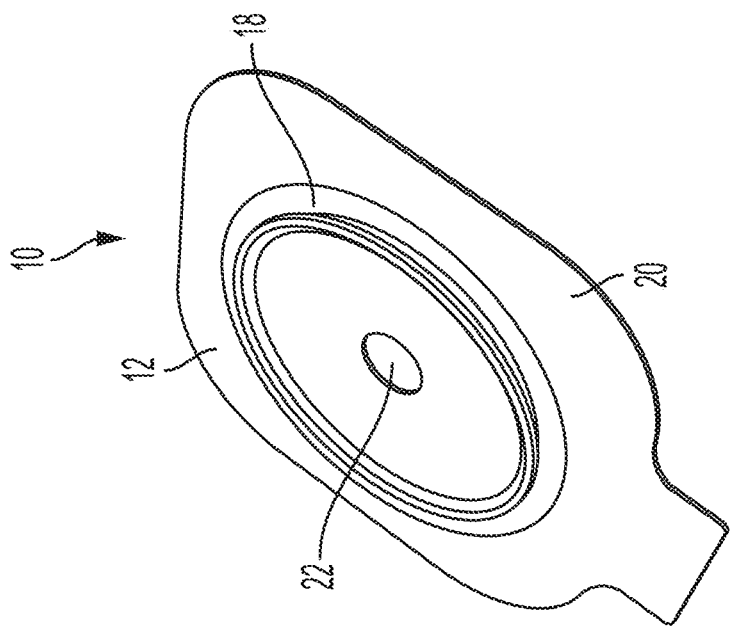
FIG. 1 is a perspective view of a pouch-facing side of an ostomy appliance, according to an embodiment.

FIG. 1 is a perspective view of a pouch-facing side of an ostomy appliance 10, according to an embodiment. FIG. 2 is a perspective view of a body-facing side of the ostomy appliance 10, according to an embodiment. In the embodiment of FIGS. 1 and 2, the ostomy appliance 10 is configured as a faceplate assembly for a two-piece ostomy pouch system for attaching an ostomy pouch 210 (FIG. 7) to a user. In other embodiments, the ostomy appliance may be configured as an ostomy barrier for a one-piece ostomy pouch system, an ostomy skin barrier ring, and the like.

The ostomy appliance 10 may be provided with a skin barrier 11 (FIG. 2) on a body-facing side 16 configured to adhere to the user's skin. The skin barrier 11 may be formed from a suitable medical grade adhesive, such as a hydrocolloid adhesive. A backing layer 12 (FIG. 1) may be provided on a pouch-facing side 20 of the ostomy appliance 10. The backing layer 12 may be formed from a soft, flexible material that is generally soft and non-irritable to the user's skin, such as a nonwoven or foam material. The ostomy appliance 10 may further include a coupling ring 18 on the pouch-facing side 20, which may be configured to engage a coupling ring 212 (FIG. 7) to attach the ostomy pouch 210 to the ostomy appliance 10.

The ostomy appliance 10 may include a stoma opening 22 extending through the backing layer 12 and the skin barrier 11. The stoma opening 22 may be configured to receive the stoma and allow for passage of stoma fluid into the ostomy pouch 210.

Figure 3:
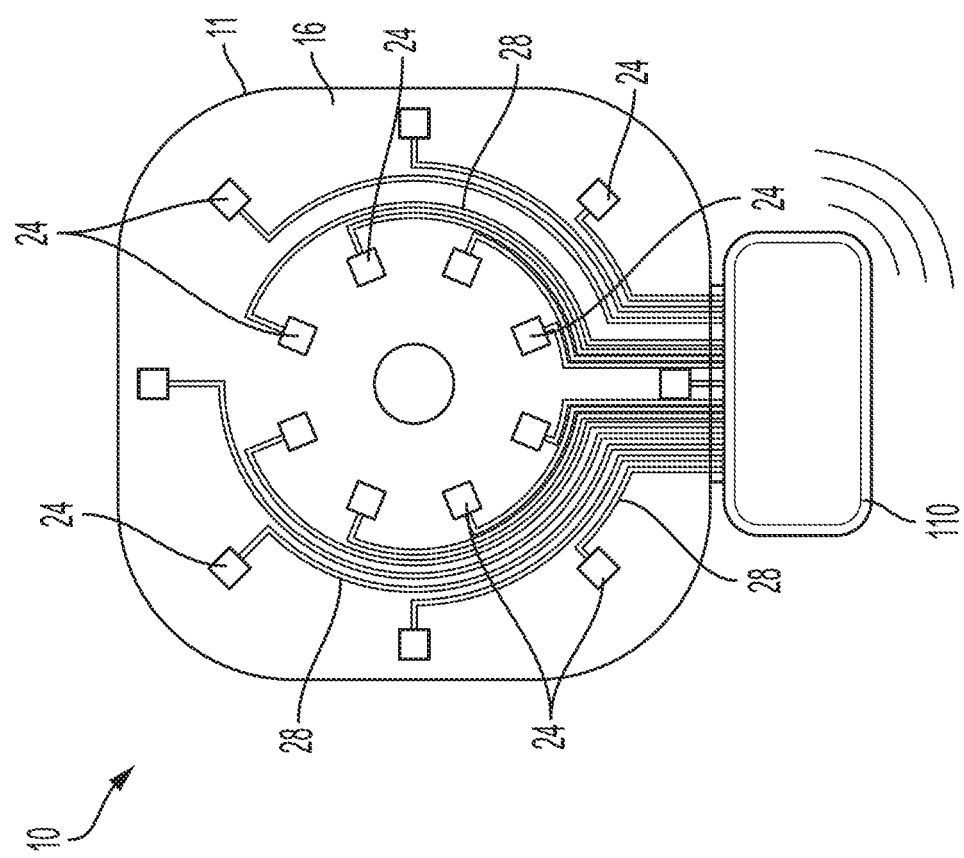
FIG. 3 is a plan view of the body-facing side of the ostomy appliance, according to an embodiment.

FIG. 3 is a plan view of the body-facing side 16 of the ostomy appliance 10, according to an embodiment. With reference to FIGS. 2 and 3, the ostomy appliance 10 may include a plurality of temperature sensors 24 configured to detect a temperature. In one embodiment, the temperature sensors 24, such as thermistors, may be embedded in the skin barrier 11. As understood in the art, thermistors are thermally sensitive resistors that exhibit a change in resistance proportional to small changes in temperature of a target object. To measure temperature using a thermistor, a voltage may be applied across the thermistor, wherein power is generated within the thermistor according to the equation, $P=(V^2)/R$, where P is power, V is voltage, and R is thermistor resistance. Any energy dissipated by the thermistor may be released as heat. In one embodiment, a circuit may be designed such that the voltage is sufficiently low and the thermistor resistance is sufficiently high to keep the heat dissipation to a negligible level. In another embodiment, a higher voltage may be placed across the thermistor to induce self-heating. In a self-heating mode, a fixed amount of power may be applied to the thermistor for a fixed period of time and the temperature rise of the thermistor over that time may be recorded. In such embodiment, fluid leak detection may be facilitated as many materials have different thermal capacitances when dry compared to when wet.

The temperature sensors 24 may be electrically connected to a first electrical interface 26 (FIG. 2) by way of electrical circuitry 28. In one embodiment, the first electrical interface 26 may include a plurality of electrical contacts 30. In one embodiment, each temperature sensor 24 may be electrically connected to a respective electrical contact 30 with respective electrical circuitry 28.

In one embodiment, the temperature sensors 24 may be positioned substantially concentric with the stoma opening 22. For example, the temperature sensors 24 may be positioned along a substantially circular path concentric with the stoma opening 22. In one embodiment, the temperature sensors 24 may be positioned different distances from the stoma opening 22. For example, the temperature sensors 24 may be positioned along different substantially circular paths of different diameters. Accordingly, in one embodiment, the temperature sensors 24 may be configured to detect temperatures at different distances from the stoma opening 22. The different paths may be substantially concentric with one another and with the stoma opening 22. In one embodiment, the temperature sensors 24 are positioned to substantially surround the stoma opening 22 at predetermined intervals within a range of approximately 360 degrees.

In FIGS. 2 and 3, it will be appreciated that although numerous temperature sensors 24, electrical circuitry 28 and electrical contacts 30, are depicted, reference numbers and lead lines identifying some of the sensors 24, circuitry 28 and contacts 30 are omitted, for clarity.

The ostomy appliance 10 may further include a wearable device 110 removably connected to the ostomy hydrocolloid 11. In one embodiment, the wearable device 110 may be removably connected to the first electrical interface 26.

FIG. 4 is a perspective view of the wearable device 110, according to an embodiment, and FIG. 5 is a cut-away perspective view of the wearable device 110 of FIG. 4, according to an embodiment. The wearable device 110 may include a housing 112 comprising one or more operating switches or buttons, such as a power switch 114.

The wearable device 110 also may include a controller 116, a power supply 118, such as a battery, a wireless transceiver 120, and optionally a first charging interface 122 for charging the power supply 118. The wearable device 110 also may include a second electrical interface 124 configured for electrical connection to the first electrical interface 26, for example, by electrical contact with the contacts 30. The controller 116, power supply 118, the wireless transceiver 120 and the second electrical interface 124 may be operably connected to one another. In one embodiment, the wearable device 110 may include a printed circuit board ("PCB") 126 to which the controller 116, the power supply 118, the wireless transceiver 120, and the second electrical interface 124, for example, may be mounted or connected.

The controller 116 may be a microcontroller and may include a processor, memory and communication module. The processor may be configured to execute program instructions stored in the memory, and the communication module may be configured to send or receive signals to and from the processor to carry out operations based on the program instructions.

In one embodiment, the wireless transceiver 120 may be configured for wireless communications according to known wireless communication standards and protocols and may communicate over known communication networks, such as personal area networks, wireless local area networks, metropolitan area networks and wide area networks. Accordingly, the wireless transceiver 120 may be configured for various wireless communications including, but not limited to, Bluetooth, Bluetooth Low Energy, Near-Field Communication, WiFi, WiMax, cellular LTE or other cellular radio communications. In one embodiment, the wireless transceiver 120 may be a Bluetooth enabled microchip.

In one embodiment, the wearable device 110 may include one or more output devices operably connected to the controller 116, such as a visual indicator 128, an audio indicator 129, or both. Alternatively, or in addition, other output devices may be envisioned as well, such as a vibrating indicator. The visual indicator 128 may include, for example, a light emitting diode (LED) or a display, such as a liquid crystal display (LCD).

FIG. 6 is a perspective view of the ostomy appliance 10 with the wearable device 110 connected thereto, according to an embodiment. The power supply 118 may provide an electrical current to the electrical circuitry 28 and the sensors 24 by way of an electrical connection between the first electrical interface 26 and the second electrical interface 124. In one embodiment, the wearable device 110 may be connected to the ostomy appliance 10, for example, by way of friction fit, interference fit, clamping, mechanical interlock, or other suitable fastening mechanism. In some embodiments, the ostomy appliance 10 and the wearable device 110 may be configured for wireless communication. In such embodiments, the wearable device 110 may be carried separately from the appliance 10 and configured to communicate remotely with the ostomy appliance 10.

In the embodiments above, the ostomy appliance 10 may be monitored for one or more conditions on the basis of thermal properties, such as temperature, detected at the temperature sensors 24. Such conditions may include, but are not limited to, stoma fluid leakage, ostomy appliance 10 to skin application, and seal degradation. In one embodiment, the controller 116 may analyze the detected temperatures to determine the condition of the ostomy appliance 10.

The detected temperatures at different temperature sensors 24 may typically correspond to a skin temperature of the user. Stoma fluid generally may have a temperature different than that of the user's skin. Thus, stoma fluid leakage may cause a change in temperature at one or more temperature sensors 24 where such leakage is present. Accordingly, in one embodiment, the controller 116 may determine that stoma fluid is leaking from the stoma opening 22 in response to a change in temperature detected at one or more of the temperature sensors 24. In one embodiment, the controller 116 may compare the detected change in temperature at a sensor 24 to a stored threshold value to determine whether stoma fluid is leaking. Conversely, the controller 116 may determine that stoma fluid is not leaking from the stoma opening 22 if a temperature change is not detected.

In one embodiment, the skin barrier 11 may be formed of, or include, a hydrocolloid material. The hydrocolloid material, when saturated by stoma fluid, for example, may transfer heat differently than when dry. Thus, a temperature detected at a sensor 24 at a wet portion of the skin barrier 14 may be different than a temperature detected at a sensor 24 at a dry portion of the skin barrier 14. Accordingly, in one embodiment, the controller 116 may compare detected temperatures at multiple sensors 24 and determine that stoma fluid is leaking from the stoma opening 22 if the detected temperature at one or more sensors 24 differs from the detected temperature at one or more other sensors 24. In one embodiment, the controller 116 may compare a difference in detected temperatures to a threshold value to determine whether stoma fluid is leaking. Conversely, the controller 116 may determine that stoma fluid is not leaking from the stoma opening 22 if detected temperatures at different sensors 24 are substantially the same.

In one embodiment, the controller 116 may also determine an extent of stoma fluid leakage. Such an extent may refer to a range over which the stoma fluid is leaking or a distance from the stoma opening 22 or other reference point over which the stoma fluid has migrated. For example, the positions of the temperatures sensors 24 on the ostomy appliance 10 may be known. In embodiment, the range of stoma fluid may be determined based on a number of temperature sensors 24 where stoma fluid leakage has been determined. A distance over which stoma fluid leakage has migrated may be determined by retrieving the known position of a temperature sensor 24 at which stoma fluid leakage has been determined.

Detected temperatures at the temperature sensors 24 may be expected to be uniform, or correspond to an expected or known profile, when the ostomy appliance 10, and in particular the skin barrier 11, is properly applied to the user's skin. In one embodiment, proper application of the ostomy appliance 10 may refer to a condition in which substantially an entire surface area of the skin barrier 11 is adhered to the user's skin.

However, in some instances, the ostomy appliance 10 may be improperly applied to the user's skin. For example, the skin barrier 11 may be non-uniformly adhered to the user's skin, such that air pockets are formed between the skin barrier 11 and the user's skin. In such a condition, the temperature sensors 24 located at the non-uniformly applied portions, may detect temperatures which are different than the temperatures detected by sensors 24 at the properly applied portions, or do not fall within the expected or known temperature profile.

Accordingly, the controller 116 may determine that the ostomy appliance 10, for example, the skin barrier 11, is improperly applied to the user's skin if the temperatures detected by the temperature sensors 24 are substantially non-uniform or fall outside of an expected or known temperature profile. Conversely, the controller 116 may determine that the ostomy appliance 10 is properly applied if the detected temperatures are substantially uniform or fall within an expected or known temperature profile. In one embodiment, the controller 116 may analyze the detected temperatures for such a condition within a predetermined time period after application of the ostomy appliance 10 to the user's skin.

A user may perspire at a location where the ostomy appliance 10 is adhered to the user's skin. In some instances, the perspiration causes the seal formed between the skin barrier 11 and the user's skin to degrade. Such seal degradation may produce a consistent decrease in temperature detected at the temperature sensors 24. In one embodiment, the controller 116 may determine that the seal has degraded to a condition where replacement is recommended based on a decrease in the detected temperature by a predetermined amount at all temperature sensors 24, or alternatively, at a predetermined number of temperatures sensors 24. Conversely, controller 116 may determine that the seal formed between the skin barrier 11 and the user's skin remains in an suitable condition if a decrease in the detected temperature does not exceed a predetermined amount at all temperatures sensors 24, or alternatively, at a predetermined number of temperature sensors 24.

Figure 7:
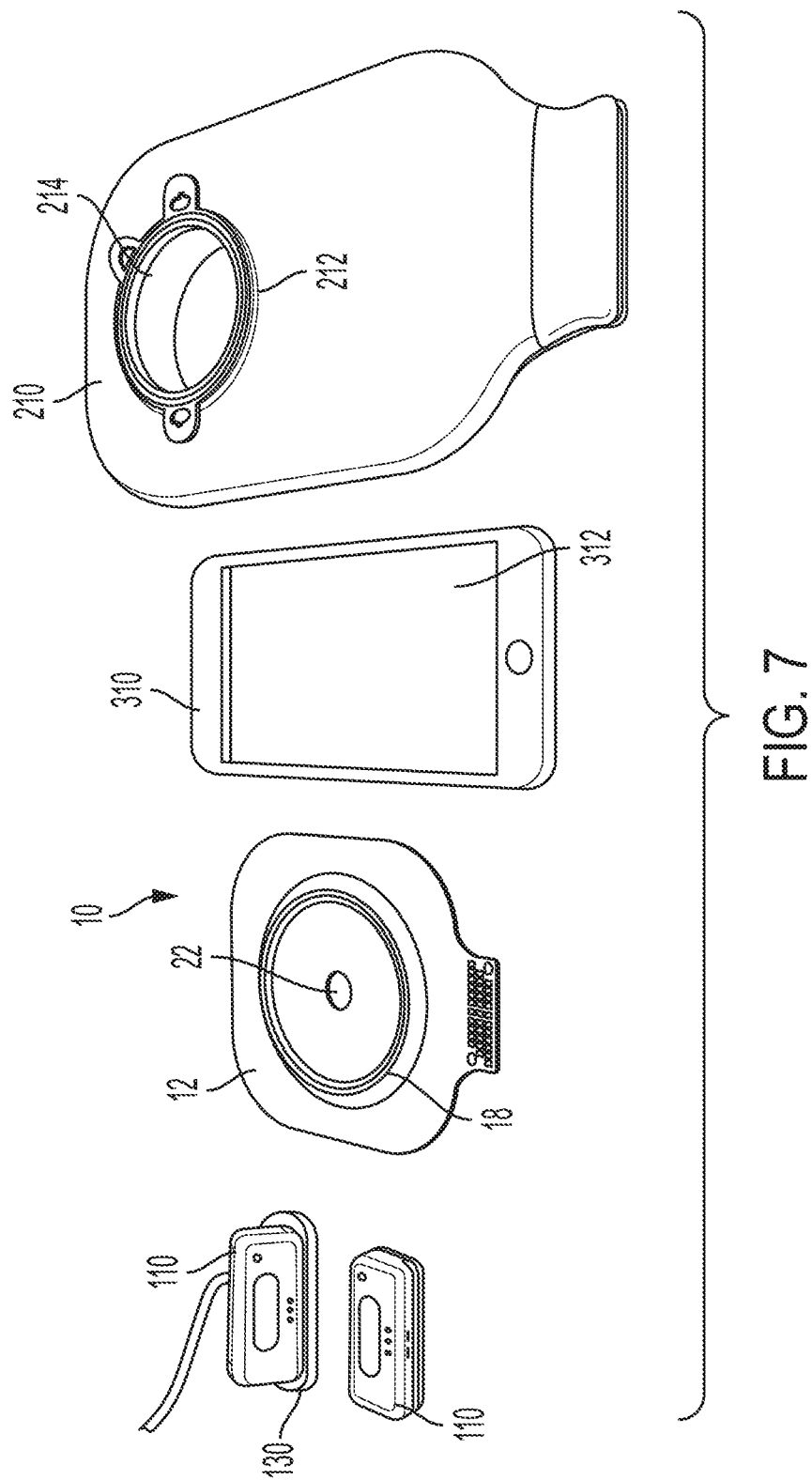
FIG. 7 shows various components of the ostomy appliance according to embodiments.

FIG. 7 shows various components for use with the ostomy appliance 10 according to embodiments. In one embodiment, a charging device 130 may have a second charging interface (not shown). The second charging interface is configured for electrical connection with the first charging interface 122 to charge the power supply 118.

The ostomy pouch 210 may be configured for coupling with the ostomy appliance 10. In one embodiment, the ostomy pouch 210 may be coupled to the ostomy appliance 10 at the coupling ring 18 by way of a corresponding pouch coupling ring 212. An inlet opening 214 may be included in the ostomy pouch 210 and may be configured for alignment with the stoma opening 22 of the ostomy appliance 10.

In one embodiment, the ostomy appliance 10 may be communicatively coupled to a personal notification device 310. In one embodiment, the personal notification device 310 may be communicatively coupled to the wearable device 110 over a wireless communication interface via the wireless transceiver 120.

In one embodiment, the personal notification device 310 may be a mobile communication device, such as a smartphone or other mobile phone. Alternatively, or in addition, the personal notification device 310 may be another mobile communication device, a portable electronic device, or other electronic device configured for communication, directly or indirectly, with the wearable device 110. Such devices may include, but are not limited to, tablets, laptop computers, desktop computers, smart speakers, connected wearable accessories such as fitness trackers, smart watches and the like, smart televisions, personal digital assistants and the like.

In one embodiment, the wearable device 110 may be paired, synced, or otherwise communicatively connected to the personal notification device 310 with a known pairing or syncing operation, which may be initiated, for example, by operation of a switch, such as the switch 114 or a separate switch, of the wearable device 110.

In one embodiment, the personal notification device 310 may include a controller, similar to the controller 116 above, and may monitor the ostomy appliance 10 for one or more conditions based on temperatures detected at the temperatures sensors 24. In one embodiment, the wearable device 110 may transmit the detected temperatures to the personal notification device 310, and the personal notification device 310 may determine the one or more conditions in the manner described above with respect to the controller 116, based on the detected temperatures received from the wearable device 110. Alternatively, or in addition, the wearable device 110 may transmit the one or more conditions determined by the controller 116 to the personal notification device 310.

In one embodiment, the wearable device 110 may be configured to output a notification based on the determined condition. For example, the controller 116 may be configured to control one or more of the output devices 128, 129 based on the determined condition, such as a leak or barrier degradation. In one embodiment, the notification may vary depending on the determined condition. For example, the notification may vary in type, frequency, intensity, volume, brightness, pattern, or the like.

Alternatively, or in addition, the personal notification device 310 may be configured to output the notification based on the determined condition. In one embodiment, the personal notification device 310 may include one or more output devices of the types described above and may control the one or more output devices to output the notification. In one embodiment, the personal notification device 310 may further include an output device formed as a display screen 312. The display screen may be configured to display a notification in the form of, for example, graphics, text, symbols, representative models of the skin barrier 11 and the like, or combinations thereof. In one embodiment, the notification may include instructions to replace the ostomy appliance 10.

In one embodiment, the personal notification device 310 may receive the determined condition, or determine the condition, of the ostomy appliance 10 at predetermined time intervals. Alternatively, or in addition, a user may operate the personal notification device 310 to request the determined condition from the wearable device 110 or to determine the condition.

In one embodiment, the personal notification device 310, embodied as a smartphone, may perform functions according to a smartphone application directed to the ostomy appliance 10. The smartphone application may include program instructions stored in a memory unit of the smartphone which are configured to be executed by a processor of the smartphone to control the smartphone to perform the functions. For example, the smartphone may be controlled to generate and output the notification. The smartphone may also be controlled to store additional data and enable further communications. For example, the smartphone may be configured to track leaks or degradation of the skin barrier 11, behaviors and activities that could potentially affect wear time, including, but not limited to: pouch changes, diet, leakage occurrence, gas occurrence and physical activity.

In one embodiment, the smartphone may be configured to provide a platform to share practices and advice from other users and clinicians. In one embodiment, the smartphone may be configured to allow for communication with other information sources, for example, to access video tutorials providing additional education and instruction on managing a stoma. In one embodiment, the smartphone may be configured to allow for pictures to be taken and stored of the stoma and skin health. In one embodiment the smartphone may be configured to facilitate contact with a wound, ostomy and continence (WOC) nurse (also referred to as an enterostomal therapy (ET) nurse), for example, to troubleshoot or share stoma and skin health conditions. In one embodiment, the smartphone may be configured to allow for ordering or automatic re-ordering of an ostomy appliance 10 or related supplies when a determination is made that such supplies are running low. In one embodiment, the smartphone may be configured to provide usage and patient data to, for example, the ostomy appliance manufacturer, such as marketing, research and product support teams. In one embodiment, such usage and data may be provided, for example, after a user opts-in, and the data may be provided securely, anonymously, and in accordance with local privacy laws and regulations, to support health economics.

Those having ordinary skill in the art will appreciate that the present disclosure is not limited to a smartphone application executed to control functions of a smartphone according to the examples above. For instance, it is also envisioned that a similar software application could be executed by a tablet or other portable device, a remote server configured to be accessed by the user through a known communications interface, or at a personal computing device, such as a laptop or desktop computer, or some combination of the above.

Figure 8C:
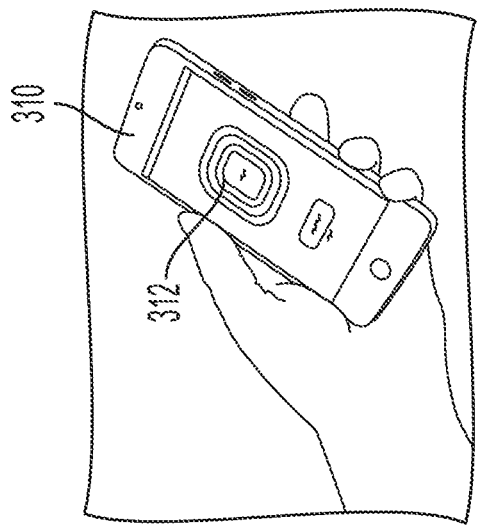
FIGS. 8A-8C show examples of a user configuring the ostomy appliance for use, according to an embodiment.
Figure 8B:
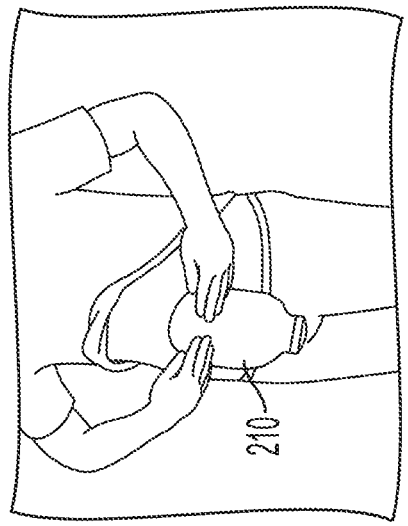
Figure 8A:
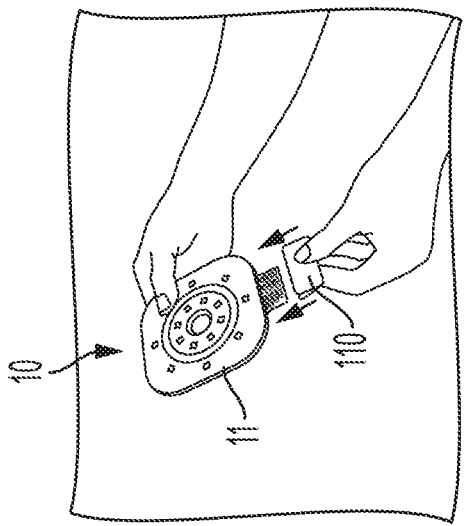

FIGS. 8A-8C show examples of a user configuring the ostomy appliance 10 for use, according to an embodiment. For example, the user may connect the wearable device 110 to the ostomy appliance 10 (FIG. 8A), attach the ostomy pouch 210 to the ostomy appliance 10 (FIG. 8B) and communicatively connect the personal notification device 310 to the wearable device 110 (FIG. 8C).

Figure 9C:
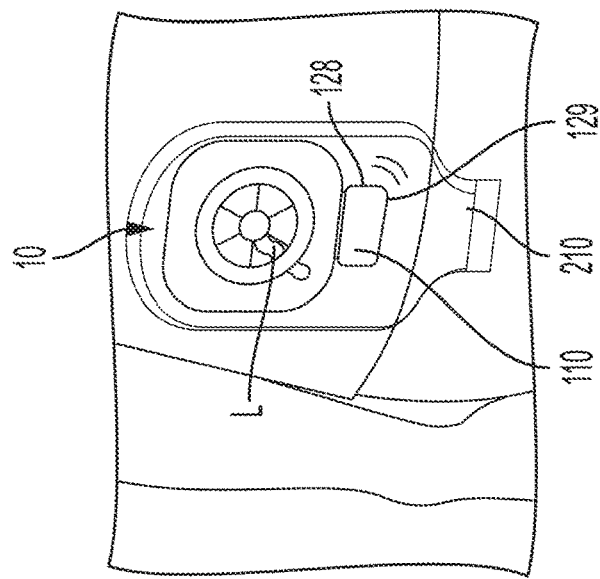
FIGS. 9A-9C show examples of a user during normal use of the ostomy appliance, according to an embodiment.
Figure 9B:
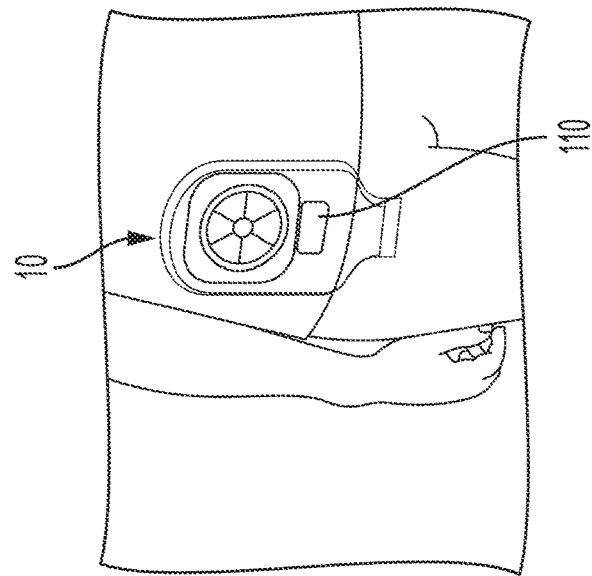
Figure 9A:
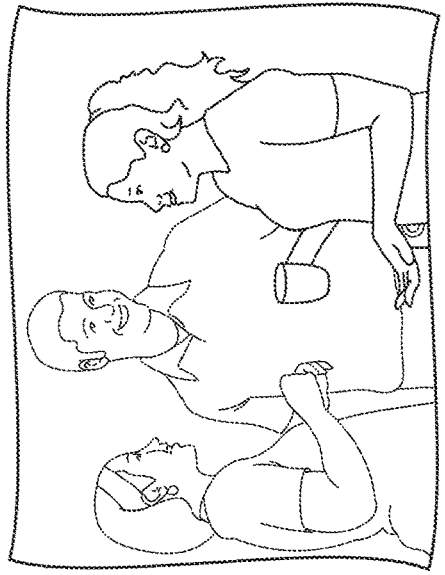

FIGS. 9A-9C show examples of a user during normal use of the ostomy appliance 10, according to an embodiment. For example, the user may interact in a social setting (FIG. 9A), the wearable device 110 may monitor a condition of the ostomy appliance 10 (FIG. 9B), and the may detect stoma fluid leakage 'L' along the ostomy appliance 10 (FIG. 9C). An output device 128, 129 may provide a notification based on a determined condition.

Figure 10C:
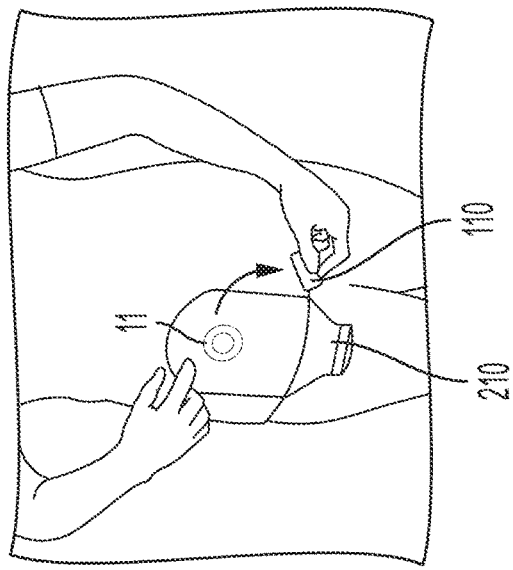
FIGS. 10A-10C show examples of a user receiving a notification of a condition and tending to the ostomy appliance, according to an embodiment.
Figure 10B:
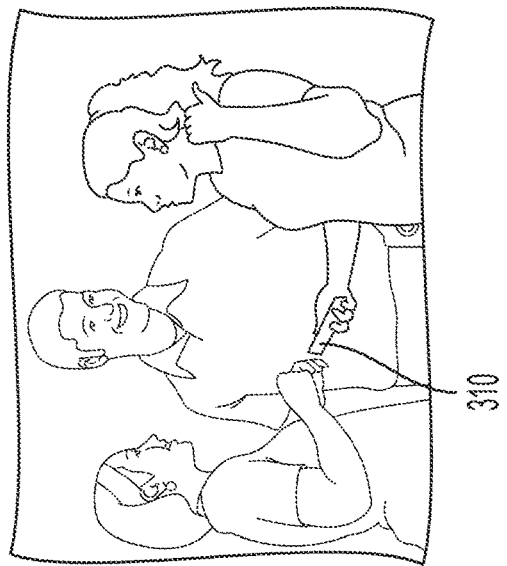
Figure 10A:
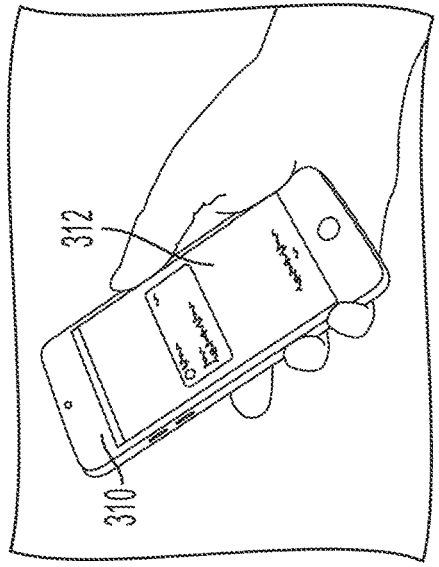

FIGS. 10A-10C show examples of a user receiving a notification of a leakage condition and tending to the ostomy appliance 10, according to an embodiment. For example, a notification of the leakage condition may be output on the personal notification device 310 (FIG. 10A), the user may move to a location to tend to the ostomy appliance 10 (FIG. 10B) and the user may remove the wearable device 110 from the ostomy appliance 10 (FIG. 10C) to replace the ostomy appliance 10.

In one embodiment, the temperature sensors 24 may not be in contact with the user's skin. Accordingly, biocompatibility issues with the sensors 24 may substantially be avoided. In addition, a thermally insulating film may be laminated on top of the temperature sensors 24 to provide higher-fidelity readings.

Figure 11:
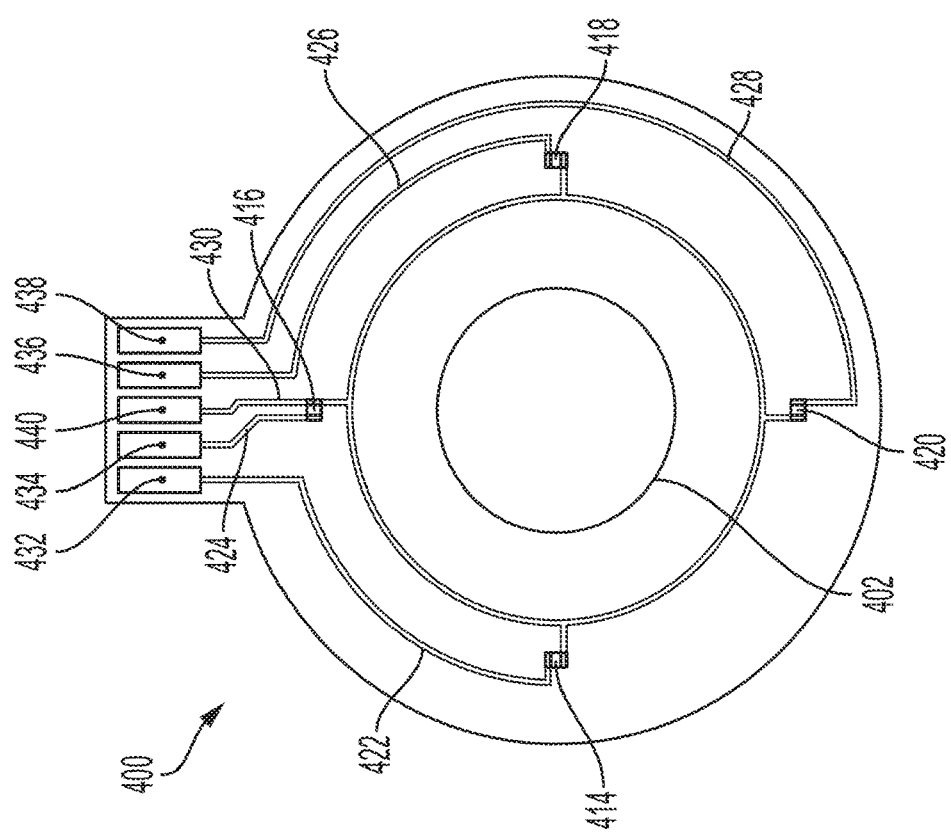
FIG. 11 is a schematic illustration of a circuit board including thermistors for an ostomy appliance, according to an embodiment.

FIG. 11 is a schematic illustration of a circuit board 400 for an ostomy appliance according to an embodiment. The circuit board 400 may be arranged on or embedded between skin barrier layers of an ostomy appliance. The circuit board may generally comprise plurality of thermistors 414, 416, 418, 420, electrical circuitry 422, 424, 426, 428, 430, and an electrical interface comprising a plurality of electrical contacts 432, 434, 436, 438, 440. The circuit board 400 may be used to make an ostomy faceplate for a two-piece ostomy pouch system, for example, the ostomy appliance 10 of FIGS. 1-3, an ostomy barrier for a one-piece ostomy pouch system, an ostomy barrier ring, and the like.

In one embodiment, the thermistors 414, 416, 418, 420 may be configured to operate in a self-heating mode. In such an embodiment, each the thermistors 414, 416, 418, 420 may transmit heat to the surrounding skin barrier. The thermal properties of the skin barrier may change when wet and exhibit a different thermal response to the heat supplied by the thermistors when compared to a thermal response of the skin barrier when dry. By applying a fixed power for a fixed duration and measuring temperature changes using the thermistors 414, 416, 418, 420 over that time, the circuit board 400 may be configured to distinguish a wet condition of the skin barrier from a dry condition of the skin barrier. The circuit board 400 may also be configured to determine certain chemical characteristics of fluid in contact with the skin barrier by monitoring thermal properties of the skin barrier via the thermistors 414, 416, 418, 420.

The thermistors 414, 416, 418, 420 may be arranged at different positions on the skin barrier or embedded in the skin barrier. In the embodiment of FIG. 11, four thermistors 414, 416, 418, 420 may be arranged at different positions surrounding a stoma opening 402. In other embodiments, less than four thermistors or more than four thermistors may be arranged at different positions on or in the skin barrier to detect at least one thermal property change of the skin barrier from exposure to fluid. The thermistors may be off-the-shelf chip resistors embedded into a circuit or may be printed using a resistive ink. The thermistors may be electrically connected to a printed circuit or wired to a single area, for example, proximate an edge of the circuit board 400, for a wireless transmission to or alerting a dongle attached thereto.

In the embodiment of FIG. 11, the thermistors 414, 416, 418, 420 may be electrically connected to the electrical contacts 432, 434, 436, 438, 440 via the electrical circuitry 422, 424, 426, 428, 430. A dongle or the wearable device 110 (FIGS. 4-7) may be attached to the electrical contacts 432, 434, 436, 438 to supply power to the thermistors 414, 416, 418, 420. As shown, the thermistor 414 may be electrically connected to an electrical contact 432 via an electrical circuit 422. The thermistor 416 may be electrically connected to an electrical contact 434 via an electrical circuit 424. The thermistor 418 may be electrically connected to an electrical contact 436 via an electrical circuit 426. Further, the thermistor 420 may be electrically connected to an electrical contact 438 via an electrical circuit 428. The thermistors 414, 416, 418, 420 also may be electrically connected to a ground 440 via an electrical circuit 430, via which remaining voltage may be lead back to the attached dongle or to the wearable device 110.

Figure 12:
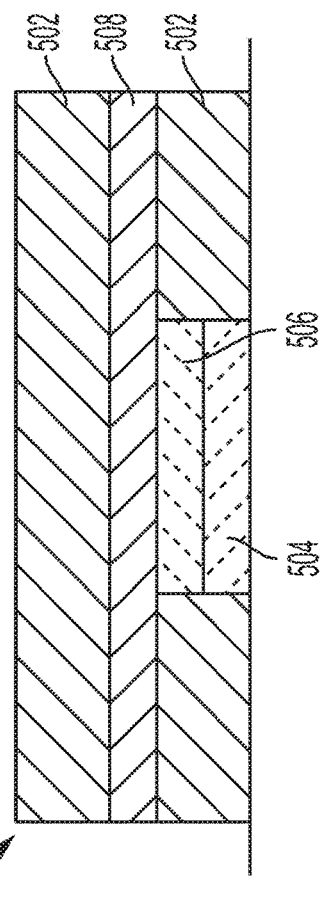
FIG. 12 is a schematic cross-sectional view of an ostomy appliance including the circuit board of FIG. 11 according to an embodiment.

In some embodiments, an ostomy appliance may include a wicking material arranged proximate the thermistors 414, 416, 418, 420 to facilitate transport of fluid toward detection areas and amplify the signal recorded by the thermistors 414, 416, 418, 420. FIG. 12 is a schematic cross-sectional view of an ostomy appliance 500 comprising a wicking material 504 according to an embodiment. The ostomy appliance 500 may include a circuit board comprising at least one thermistor 506 and an electrical circuit 508, wherein the circuit board may be configured similarly to the circuit board 400 of FIG. 11. In an embodiment, the circuit board 400 may be arranged between two layers of skin barrier layers 502 to form the ostomy appliance 500, which may be a barrier ring. The thermistor 506 and the wicking material 504 may be embedded in the skin barrier 502 formed from a suitable skin barrier material, such as hydrocolloid. The wicking material 504 may be arranged adjacent the thermistor 506 proximate a skin-contact surface of the skin barrier 502, such that the wicking material 504 may be in contact with user's skin when the ostomy appliance 500 is attached to a user. The electrical circuit 508 may be arranged adjacent the thermistor 506 opposite the wicking material 504, such that the thermistor 506 may be arranged between the wicking material 504 and the electrical circuit 508. Further, the electrical circuit 508 may be covered by a layer of the skin barrier 502 to provide a wicking material 504/thermistor 506/electrical circuit 508/skin barrier 502 construction as shown in FIG. 12.

In an embodiment, a leak detection system for an ostomy appliance may include a plurality of thermistors, which may be configured to operated in a self-heating mode at one or more polling frequencies. In such an embodiment, the leak detection system may apply a voltage to the thermistors periodically. In a self-heating operating mode, a voltage greater than a minimum power necessary for the thermistors to measure temperature may be applied to the thermistors, wherein the excess electrical energy may be converted to heat to increase the temperature of the thermistors. The thermistors may be configured to transfer heat to the surrounding environment, such as a hydrocolloid adhesive and a wicking material. The degree of a temperature change from the heat transfer may depend on the properties of the thermistors and the surrounding environment. For example, a heat capacity of a hydrocolloid adhesive may be greater when wet than dry, such that a temperature change of the hydrocolloid adhesive from the heat transfer from the thermistors may be smaller when wet than dry. In such an embodiment, the leak detection system may be configured to determine a leak based on the difference in the temperature change measured by the thermistors.

The leak detection system may be configured to apply a voltage to the plurality of thermistors for a brief period, for example, one second, at a predetermined frequency. The frequency of the voltage application to the thermistors, which is also referred to herein as a polling frequency, may be selected according to monitoring needs. A higher polling frequency may allow for a quicker response to leak events but may increase power consumption of the leak detection system.

Figure 14:
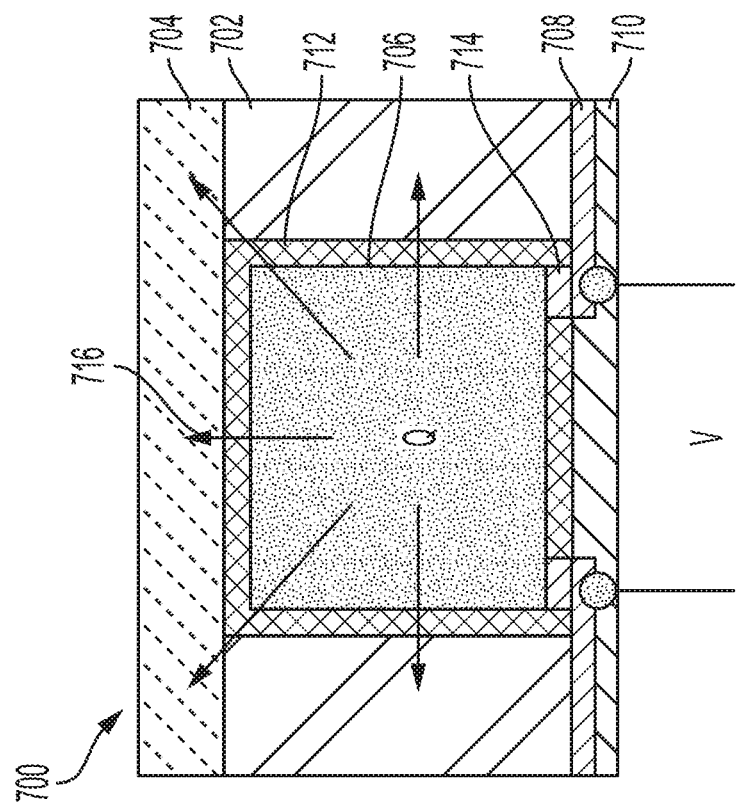
FIG. 14 is a schematic illustration of an ostomy appliance including a leak detection system including coated thermistors according to another embodiment.
Figure 13:
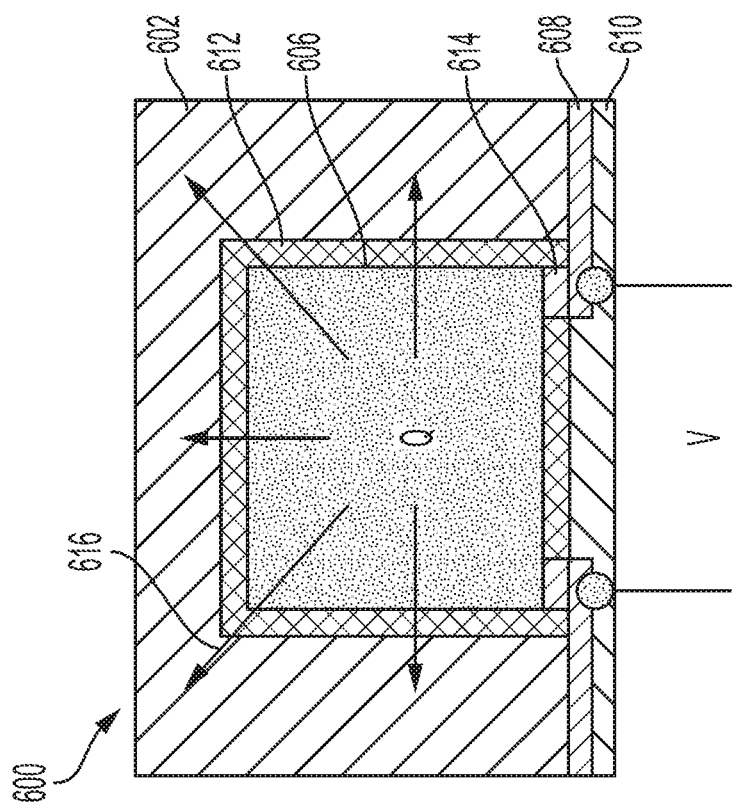
FIG. 13 is a schematic illustration of an ostomy appliance including a leak detection system including coated thermistors according to an embodiment.

In some embodiments, each of the plurality of thermistors may be coated with a suitable thermally conductive material. FIG. 13 is a schematic illustration of an ostomy appliance 600 including coated thermistors 606 according to an embodiment. The ostomy appliance 600 may generally include a skin barrier 602 formed from a hydrocolloid material and a leak detection system comprising a plurality of thermistors 606 and a sensor circuit 608 provided on a substrate 610. Each of the plurality of thermistors 606 may be coated with a conformal coating 612 and electrically connected to the sensor circuit 608 via a thermistor lead 614. In the embodiment of FIG. 14, an ostomy appliance 700 may be configured similar to the ostomy appliance 600 of FIG. 13 comprising a skin barrier 702 and a leak detection system, except the ostomy appliance 700 may also include a wick 704 configured to contact user's skin. The leak detection system may comprise a plurality of thermistors 706, wherein each of the plurality of thermistors 706 is coated with a conformal coating 712 and electrically connected to a sensor circuit 708 provided on a substrate 710 via a thermistor lead 714. The plurality of thermistors 606, 706 may be formed from known thermistors available in the market. In an embodiment, each of the plurality of thermistors 606 may be formed from a 100Ω resistor, such as the thermistors available from TDK Corporation under part number NTCG103EH101JT1.

The conformal coating 612, 712 may be configured to insulate the thermistor lead 614, 714 to prevent a short circuit and to improve the accuracy of temperature measured by the plurality of the thermistors 606, 706. In a self-heating operating mode, the leak detection system may apply a voltage (V) to the plurality of thermistors 606, 706, wherein some of the voltage may be converted to heat (Q) and transferred to the surrounding environment 602, 702, 704 as illustrated by the arrows 616, 716 in FIGS. 13 and 14. As such, the conformal coating 612, 712 may also be configured such that it does not interfere with heat transfer from the plurality of thermistors 606, 706 to the surrounding environment 602, 702, 704. The conformal coating 612, 712 may be formed from a suitable thermally conductive polymeric material.

In an embodiment, the plurality of thermistors 606, 706 may be coated with the conformal coating 612, 712 formed from a blend of urethane oligomer and (meth)acrylate monomer available under the trade name DYMAX® 1184-M-B from Dymax Corporation. The conformal coating 612, 712 may have a relatively thin thickness, such that the heat capacity of the thermistors 606, 706 does not increase substantially by the presence of the conformal coating 612, 712. In an embodiment, the conformal coating 612, 712 may have a thickness of about 10 microns to about 500 microns, preferably about 15 microns to about 200 microns, and more preferably about 20 microns to about 100 microns.

The leak detection system may be configured such that a temperature change ($\Delta T$) measured by the plurality of thermistors 606, 706 operating in a self-heating mode is sufficiently high when the surrounding environment 602, 702, 704 is dry to allow for a measurable difference in $\Delta T$ when the surrounding environment 602, 702, 704 becomes wet. Further, the $\Delta T$ for a dry surrounding environment 602, 702, 704 may be configured to minimize power consumption by the leak detection system, to minimize any alteration of the surrounding environment materials, e.g. the hydrocolloid materials 602, 702, and the wick 704, due to the application of a voltage or the $\Delta T$, and to minimize perceptibility of the voltage or the $\Delta T$ by a user. In an embodiment, the leak detection system may be configured such that a $\Delta T$ measured by each of the thermistors 606, 706 when the surrounding environment 602, 702, 704 is dry is about 4° C. to about 12° C., preferably about 6° C. to about 11° C., and more preferably about 8° C. to about 10° C.

The leak detection system may be configured to operate at one or more polling frequencies. In an embodiment, the leak detection system may be configured to operate at a polling frequency of about once every 15 seconds to about once every 30 minutes, preferably once every 30 seconds to about 15 minutes, and more preferably once about 1 minute to once about 10 minutes. The duration of a voltage application at each polling may be about 0.5 seconds to about 5 seconds, preferably about 0.7 seconds to about 3 seconds, and more preferably about 1 second to 2 seconds. For example, the leak detection system may be configured to apply a predetermined voltage for 1 second at a polling frequency of about once every 30 seconds when a risk of leakage is relatively high and a polling frequency of about once every 5 minutes when the risk of leakage is relatively low. In some embodiments, the leak detection system may be configured such that a user may adjust the polling frequency according to monitoring needs. For example, the user may set the leak detection system to operate at a polling frequency of about once every 30 seconds when engaged in a public activity, and change the setting to about once every 5 minutes when at home.

Figure 15:
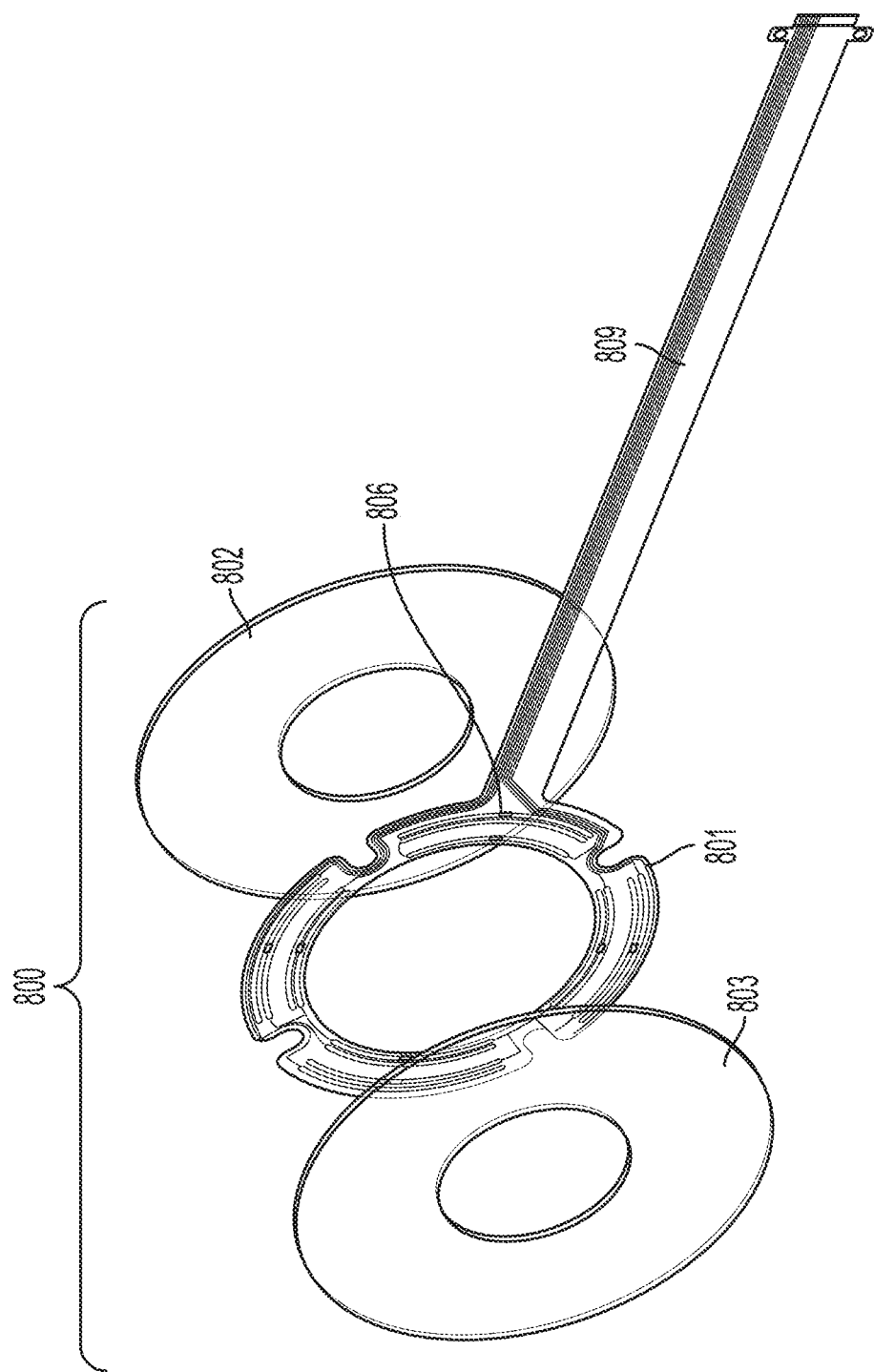
FIG. 15 is an exploded illustration of an ostomy appliance including a leak detection system according to an embodiment.

Referring to FIGS. 15 and 16, an ostomy appliance 800 may comprise a leak detection system 801 arranged between outer layers 802, 803 according to an embodiment. A first outer layer 802 may be formed from a suitable skin barrier material, such as a hydrocolloid adhesive. A second outer layer 803 may also be formed from a suitable barrier material, such as a hydrocolloid material, or a suitable backing material, such as a nonwoven, a foam, a flexible polymeric material, and the like. The leak detection system 801 may be configured similar to the leak detection systems of FIGS. 13 and 14 comprising a plurality of thermistors 806 and a sensor circuit 808 provided on a substrate 810. Each of the plurality of thermistors 806 may be coated with a conformal coating and electrically connected to the sensor circuit 808 via a thermistor lead. The leak detection system 801 may include a tail portion 809 for connecting to a controller device, such as the wearable device 110 (FIGS. 4 and 5.)

The leak detection system 801 may be configured to operate the plurality of thermistors 806 in a self-heating mode at one or more polling frequencies, such that a $\Delta T$ measured by each of the thermistors 806 when the outer layer 802 is dry is about 5° C. to about 10° C. Test samples of the leak detection system 801 were made and tested. In a test run, each of the thermistors 806 measured a $\Delta T$ of about 7.5° C. to about 9° C. when the outer layer 802 formed from a hydrocolloid material was dry and measured a $\Delta T$ of about 6° C. to about 8° C. when the outer layer 802 became wet indicating a leakage by a drop in $\Delta T$ of about 1° C. to about 1.5° C.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular. In additions, various features described with respect to any of the embodiments above may be used together, implemented in, or replace features in any of the other embodiments described above.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy appliance comprising:
 a skin barrier; and
 a leak detection system attached to the skin barrier, the leak detection system comprising:
  at least one thermistor configured to operate in a self-heating mode to measure a change in temperature ($\Delta T$) of the ostomy appliance; and
  a first electrical interface, wherein the at least one thermistor is connected to the first electrical interface via an electrical circuitry.

2. The ostomy appliance of claim 1, wherein the leak detection system is configured to apply a voltage to the at least one thermistor at one or more polling frequencies, wherein the at least one thermistor is configured to transfer heat to the skin barrier, wherein a heat capacity of the skin barrier is greater when the skin barrier material is wet than dry, wherein the $\Delta T$ of the skin barrier when dry is greater than when wet, and wherein the leak detection system is configured to determine a leak based on a drop in the $\Delta T$ of the skin barrier.

3. The ostomy appliance of claim 1, wherein the ostomy appliance further includes at least one wicking material arranged proximate the at least one thermal sensor, wherein the leak detection system is configured to apply a voltage to the at least one thermistor at one or more polling frequencies, wherein the at least one thermistor is configured to transfer heat to the wicking material, wherein a heat capacity of the wicking material is greater when the wicking material is wet than dry, wherein the $\Delta T$ of the wicking material when dry is greater than when wet, and wherein the leak detection system is configured to determine a leak based on a drop in the $\Delta T$ of the wicking material.

4. The ostomy appliance of claim 1, wherein the leak detection system is configured to transfer heat to measure the $\Delta T$ of about 6° C. to about 11° C. when the ostomy appliance is dry.

5. The ostomy appliance of claim 1, wherein the leak detection system is configured to operate at a polling frequency of about once every 30 seconds to once every 15 minutes, wherein the leak detection system is configured to apply a voltage to the at least one thermistor for a duration of about 1 second at the polling frequency.

6. The ostomy appliance of claim 5, wherein the leak detection system is configured to allow a user to set and change the polling frequency.

7. The ostomy appliance of claim 1, wherein the at least one thermistor is embedded in the skin barrier.

8. The ostomy appliance of claim 1, wherein the at least one thermistor includes a plurality of thermistors operating in a self-heating mode, wherein the ostomy appliance includes a plurality of wicking materials, wherein the plurality of thermistors and the plurality of wicking materials are embedded in the skin barrier, wherein each of the plurality of wicking materials is arranged adjacent each of the plurality of thermistors, such that each of the plurality of wicking materials is in contact with user's skin when the ostomy appliance is attached to a user; wherein an electrical circuit is provided adjacent each of the plurality of thermistors.

9. The ostomy appliance of claim 1, wherein the at least one thermistor is coated with a conformal coating.

10. The ostomy appliance of claim 9, wherein the conformal coating has a thickness of about 20 microns to about 100 microns.

11. The ostomy appliance of claim 9, wherein the conformal coating is formed from a blend of urethane oligomer and (meth)acrylate monomer.

12. The ostomy appliance of claim 1, wherein the ostomy appliance includes a stoma opening for receiving a stoma, wherein the at least one thermistor includes a plurality of thermistors, and wherein the plurality of thermistors are positioned along a path concentric with the stoma opening.

13. The ostomy appliance of claim 1, wherein the ostomy appliance includes a stoma opening for receiving a stoma, wherein the at least one thermistor includes a plurality of thermistors, and the plurality of thermistors are positioned along a plurality of paths concentric with the stoma opening, wherein the plurality of paths are disposed at different distances from the stoma opening.

14. The ostomy appliance of claim 1, wherein the ostomy appliance is a faceplate for a two-piece ostomy pouch system including a body-side coupling ring configured to engage with a pouch-side coupling ring provided on an ostomy pouch to attach the ostomy pouch to the faceplate, or an ostomy skin barrier appliance for a one-piece ostomy pouch system attached to an ostomy pouch, or an ostomy skin barrier ring.

15. The ostomy appliance of claim 1, wherein the skin barrier is formed from a hydrocolloid adhesive.

16. The ostomy appliance of claim 1, further comprising a wearable device removably and operably connected to the leak detection system, the wearable device comprising:
 a housing;
 a second electrical interface configured for electrical connection to the first electrical interface;
 a power supply; and
 a controller operably connected to the power supply.

17. The ostomy appliance of claim 16, wherein the controller is configured to determine an ostomy effluent leakage condition based on a change in $\Delta T$ from exposure to an ostomy effluent or an ostomy appliance detachment condition based on a change in $\Delta T$ due to detachment of the skin barrier from a user.

18. The ostomy appliance of claim 17, wherein the wearable device further comprises one or more output devices operably connected to the controller and configured to output a notification based on the determined condition.

19. The ostomy appliance of claim 1, wherein the wearable device further comprises a wireless transceiver.

20. The ostomy appliance of claim 19, further comprising a personal communication device communicatively connected to the wearable device via the wireless transceiver.

21. The ostomy appliance of claim 20, wherein the personal communication device is configured to output a notification based on a condition of the ostomy appliance.

22. The ostomy appliance of claim 20, wherein the personal communication device is a smartphone.

* * * * *